(12) United States Patent
Matsutani et al.

(10) Patent No.: US 7,977,603 B2
(45) Date of Patent: Jul. 12, 2011

(54) METHOD OF MANUFACTURING AN EYELESS SUTURE NEEDLE

(75) Inventors: Kanji Matsutani, Tochigi (JP); Masaki Mashiko, Tochigi (JP); Yuji Yokoyama, Tochigi (JP); Mieko Akaba, Tochigi (JP); Hiroshi Yagisawa, Tochigi (JP); Masao Akatsuka, Tochigi (JP); Shoichi Fukuda, Tochigi (JP)

(73) Assignee: MANI., Inc., Tochigi (JP)

( * ) Notice: Subject to any disclaimer, the term of this patent is extended or adjusted under 35 U.S.C. 154(b) by 666 days.

(21) Appl. No.: 11/392,803

(22) Filed: Mar. 30, 2006

(65) Prior Publication Data

US 2006/0219677 A1  Oct. 5, 2006

(30) Foreign Application Priority Data

Mar. 31, 2005  (JP) .................... 2005-101965

(51) Int. Cl.
*B23K 26/00* (2006.01)

(52) U.S. Cl. ............ 219/121.71; 219/121.7; 219/121.66

(58) Field of Classification Search ............ 219/121.71, 219/121.7, 121.66, 121.65, 121.85; 29/558
See application file for complete search history.

(56) References Cited

U.S. PATENT DOCUMENTS

| | | | | |
|---|---|---|---|---|
| 4,054,144 A | * | 10/1977 | Hoffman et al. | 606/227 |
| 4,060,885 A | * | 12/1977 | Hoffman et al. | 29/407.08 |
| 4,072,041 A | * | 2/1978 | Hoffman et al. | 72/416 |
| 4,700,043 A | * | 10/1987 | Matsutani | 219/121.69 |
| 4,805,292 A | * | 2/1989 | Noguchi | 29/445 |
| 5,012,066 A | * | 4/1991 | Matsutani et al. | 219/121.68 |
| 5,353,624 A | * | 10/1994 | Matsutani | 72/413 |
| 5,417,710 A | * | 5/1995 | Matsutani et al. | 606/224 |
| 5,889,255 A | * | 3/1999 | Bogart et al. | 219/121.65 |
| 5,903,966 A | * | 5/1999 | Sonderegger | 29/464 |
| 6,018,860 A | * | 2/2000 | Smith et al. | 29/558 |
| 6,252,195 B1 | * | 6/2001 | Mosavi et al. | 219/121.69 |
| 2001/0022296 A1 | * | 9/2001 | Mosavi et al. | 219/121.71 |

FOREIGN PATENT DOCUMENTS

JP  2001-8942 A  1/2001

* cited by examiner

*Primary Examiner* — M. Alexandra Elve
(74) *Attorney, Agent, or Firm* — Orion Consulting, Ltd.; Joseph P. Farrar

(57) ABSTRACT

A method for manufacturing an eyeless needle by which a satisfactory hole can be formed in the end surface of a fine suture needle having a needle diameter less than 150 micrometers is proposed.

In a method for manufacturing an eyeless needle by forming a hole for inserting and fixing one end of a suture thread by caulking in the end surface of the eyeless suture needle made of stainless steel, the hole is formed by irradiating the end surface of a needle material thicker by 6 to 20 micrometers than a desired needle diameter of the suture needle less than 150 micrometers with one shot of a laser beam, and subsequently, a portion thicker than the desired needle diameter is removed by electrolytic polishing or chemical polishing.

2 Claims, 3 Drawing Sheets

Fig. 4
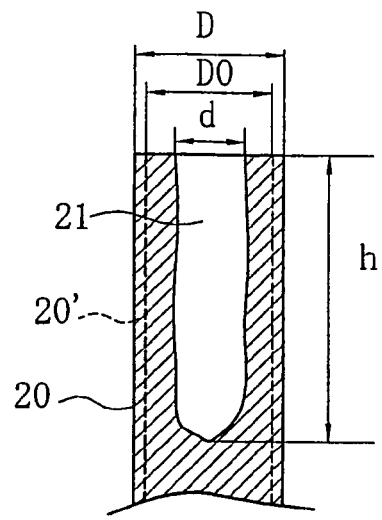
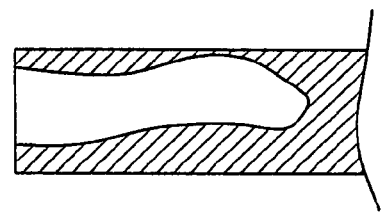
Fig. 5A
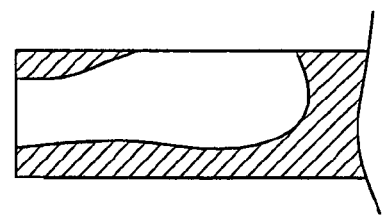
Fig. 5B
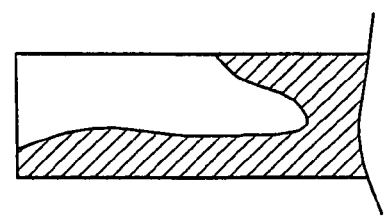
Fig. 5C

METHOD OF MANUFACTURING AN EYELESS SUTURE NEEDLE

BACKGROUND OF THE INVENTION

1. Field of the Invention

The present invention relates to a method for manufacturing a suture needle for medical use, and particularly, to a method for manufacturing a fine eyeless suture needle having a needle diameter less than 150 micrometers.

2. Background of the Invention

In a surgical eyeless suture needle, a hole of a predetermined depth is formed in the end surface on a base side along the axial center, and the end of a suture thread is inserted into the hole and set by caulking in the suture needle.

As the hole machining methods of the surgical eyeless suture needle, methods, such as drilling, electrical discharge machining, and laser beam machining, are conventionally used.

In the case of the drilling and the electrical discharge machining, a drill and a discharge electrode having the same diameter as a hole diameter are used. Therefore, if a needle diameter is reduced, it is necessary to reduce the diameter of the drill, and the diameter of the electrode in accordance with the needle diameter. In the case of a small needle diameter equal to or less than 0.3 mm, a drill and an electrode thinner than the needle diameter are required, and the manufacturing thereof becomes difficult.

On the other hand, in the case of the laser beam machining, tools, such as the drill and the electrode, are not required at all, and an extremely small hole can be formed. According to this machining method, a portion serving as the hole of a needle material is instantaneously heated with the energy of laser beams, and sublimated to form a hole.

However, the hole formation machining of the eyeless suture needle, and in particular hole formation machining for an eyeless suture needle having extremely small needle diameter less than 150 micrometers, poses various problems compared with other general laser beam machining.

For example, when a hole of a diameter of 60 micrometers is formed in a needle material having a needle diameter of 100 micrometers, the thickness of the hole wall is only 20 micrometers. The depth of the hole is required to be 8 to 15 times as large as the hole diameter. When the hole diameter is 60 micrometers, the depth of the hole is 480 to 900 micrometers. The hole must not be a pierced hole visible from the outside, but a dead-end hole not seen from the outside except an entrance.

Accordingly, when a hole is formed in a suture needle having a needle diameter less than 150 micrometers, it is extremely difficult to keep the diameter, depth, and shape of the hole constant, and the suture needle of the above size is not manufactured by other manufacturers, or a hole part is lengthened in a plate shape and caulked so as to wrap the suture thread. However, according to this method, since the caulked part is long and stepped, and further, the caulking is performed by force, an opened line is formed on a boundary line between the caulked portion of the needle material where the suture thread is fixed and the anterior portion, which opened line easily causes damage to body tissues. In the case of the laser beam machining, a material sublimated by laser beams must be dispersed outside the hole. However, there occurs sometimes a so-called sputtering phenomenon that the material which is not dispersed adheres to the inner wall of the hole and solidifies, and the material fills the hole, which makes insertion of the suture thread difficult.

FIGS. 5A, B, and C are examples of defective hole formation, wherein FIG. 5A shows an example of hole bending, FIG. 5B shows an example of a pierced hole, and FIG. 5C shows an example of hole rupture. In the case of the hole bending of FIG. 5A, a suture thread cannot be inserted into the inner part of the hole, and a suture thread of sufficient length cannot fixed by caulking. Moreover, there is a part where the inner wall became thin, and the part may be torn before use. The pierced hole of FIG. 5B shows a state where a side part of the inner part of the hole has melted and opened, and the hole rupture of FIG. 5C shows a state where a side part has melted and been lost from the entrance portion to the inner part of the hole. The suture thread cannot be fixed by caulking in the cases of FIGS. 5B and 5C. Since the suture thread is exposed from caulked holes, even if the suture thread can be fixed by caulking, the suture thread cannot smoothly pass through body tissues. The following is known as a cause of such defective hole formation.

When a hole diameter is large compared with a needle diameter, the outside thickness of the hole is greatly deflected and one side becomes thin even when the center of the hole is shifted only slightly from the center of a needle material. When laser beams are radiated, temperature at the thin part rapidly rises, the thin part melts, and the hole bending, the pierced hole, the hole rupture, or the like occurs.

When the needle diameter is reduced, the ratio of the hole diameter increases, the inner wall becomes thin, and the above-mentioned phenomenon tends to occur. When the needle diameter becomes small, the laser beam irradiation of even only one pulse is excessive, and the entire base end part may be melted and lost.

In view of the above instances, a patent document 1 (JP. A. 1988-140789) proposes a method for keeping the diameter, depth, and shape of a hole constant. This is a method for forming the hole by providing an electric shutter opened and closed by electric signals between a laser oscillator and the base end part of a suture needle, cutting the rising edge portion and falling edge portion of the output of a laser beam, and transmitting only the stable middle portion of the laser beam. According to this method, strength of the laser beam radiated to the base end part of the suture needle can be kept constant since only the stabilized portion among the pulses of the laser beam is used. As a result, satisfactory hole formation without the hole bending, the pierced hole, and the hole rupture is achieved for an eyeless suture needle having a needle diameter of approximately 300 micrometers. Moreover, hole clogging due to sputtering can also be prevented.

However, when the needle diameter is thinner than 150 micrometers, no satisfactory hole could be formed according to the hole formation by the laser beam and electric shutter of the above patent document 1. This is caused by the outside thickness of the hole becoming thin since the needle diameter becomes small, and heat capacity is reduced. Since the heat capacity of the outside of the hole is reduced, a pierced hole having a melted and lost wall tends to be produced even when the hole is formed, or sputtering occurs and the hole tends to be clogged. Therefore, no satisfactory hole could be formed by the method using only the stabilized portion among the pulses of the laser beam as described in the patent document 1.

If the optical axis of the laser beam is not coincident with the center of the end surface of the needle material as mentioned above, the wall melts due to decentering, which causes the pierced hole. Therefore, the laser beam machining is performed by using a machining laser beam after confirmation of the position of the end surface of a needle material with a microscope or the like while using visible laser beams, and then positioning. However, the stability of the output of the laser beam is adversely affected when an optical element is in the optical path of the machining laser beam.

Accordingly, a patent document 2 (JP. A. 1988-171235) aims at the stabilization of the output of a laser beam by adopting a configuration of placing a needle material on one side of a machining laser oscillator, providing a visible laser oscillator on the other side, and without providing any optical element of the visible laser oscillator in the optical path of a machining laser beam.

SUMMARY OF THE INVENTION

The present invention is made in view of the above instances, and an objective of the present invention is to propose a method for manufacturing an eyeless needle by which a satisfactory hole can be formed in the end surface of a thin suture needle having a needle diameter less than 150 micrometers.

In order to achieve the above objective, the first invention according to the present application is characterized in that, in a method for manufacturing an eyeless needle by forming a hole for inserting and fixing one end of a suture thread by caulking in the end surface of the eyeless suture needle made of stainless steel, the hole is formed by irradiating the end surface of a needle material thicker by 6 to 20 micrometers than a desired needle diameter of the suture needle less than 150 micrometers with one shot of a laser beam, and then, a portion thicker than the desired needle diameter is removed.

A method for removing the thicker portion is not particularly limited, and barrel finishing may be adopted. However electrolytic polishing or chemical polishing is suitable.

The second invention according to the present application is characterized in that, in a method for manufacturing an eyeless needle by forming a hole for inserting and fixing one end of a suture thread by caulking in the end surface of the eyeless suture needle made of stainless steel, the hole is formed by irradiating the end surface of a needle material having a desired needle diameter less than 150 micrometers with one shot of laser beam having a total pulse width equal to or less than 35 microseconds.

The third invention according to the present application is characterized in that, in a method for manufacturing the eyeless needle by forming a hole for inserting and fixing one end of a suture thread by caulking in the end surface of the eyeless suture needle made of stainless steel, the hole is formed by irradiating the end surface of a needle material having a desired needle diameter of less than 150 micrometers with a laser beam formed of a plurality of minute width pulses.

According to the above first invention, the following operations are obtained.

The one shot of the laser beam is emitted from a laser oscillator. The laser beam is converted into a laser beam having a desired minute width pulse by an electric shutter, and radiated to the end surface of the needle material thicker by 6 to 20 micrometers than the desired needle diameter less than 150 micrometers. The portion of the needle material irradiated with the laser beam instantaneously reaches a high temperature, is sublimated, and a hole of the desired diameter and depth is formed. Since the hole is formed in the needle material thicker by a fixed amount than the desired needle diameter, heat capacity is not reduced because of reduced wall thickness, and neither hole bending nor a pierced hole is caused. Subsequently, the outside is polished by chemical polishing or electrolytic polishing to form an eyeless suture needle having the desired needle diameter. A result obtained after the polishing can be kept in a good condition by making the amount of polishing at that time 6 to 20 micrometers, that is, amount added to the desired needle diameter.

According to the above second invention, the following operations are obtained.

The one shot of the laser beam is emitted from a laser oscillator. The laser beam is converted into a laser beam having a total pulse width equal to or less than 35 microseconds by an electric shutter, becoming a desired laser beam, and radiated to the end surface of the needle material. The portion of the needle material irradiated with the laser beam instantaneously reaches a high temperature and is sublimated. Since the irradiation time by the laser beam of the minute width pulse is equal to or less than 35 microseconds, the hole of a desired diameter and depth is formed without causing a pierced hole and hole bending.

According to the third invention, the following operations are obtained.

The one shot of the laser beam is emitted from a laser oscillator. The laser beam is converted into a laser beam of minute pulse width by an electric shutter, and radiated to the end surface of the needle material. The end surface of the needle is melted by the first or second shot of a minute pulse, the surface is made uniform, and a hole is formed by subsequent minute pulses.

According to the present invention, such an excellent effect is brought about that a hole having a desired hole diameter and depth can be stably formed in a suture needle with a thickness equal to or less than 150 micrometers. By converting a laser beam into a plurality of minute width pulses, the deformation of a hole entrance is reduced, the adhesion of sputters is hardly caused, and variation can be reduced.

Other features, objects and advantages of the present invention will be apparent from the following description when taken in conjunction with the accompanying drawings, in which like reference characters designate the same or similar parts throughout the figures thereof.

BRIEF DESCRIPTION OF THE DRAWINGS

FIG. 4 is an enlarged sectional view showing the base end of a needle material with a formed hole, FIG. 5A shows an example of hole bending, FIG. 5B shows an example of a pierced hole, and FIG. 5C shows an example of hole rupture.

DETAILED DESCRIPTION OF THE PREFERRED EMBODIMENTS

In the following, an embodiment of the present invention is described with reference to the accompanying drawings.

Figure 1:
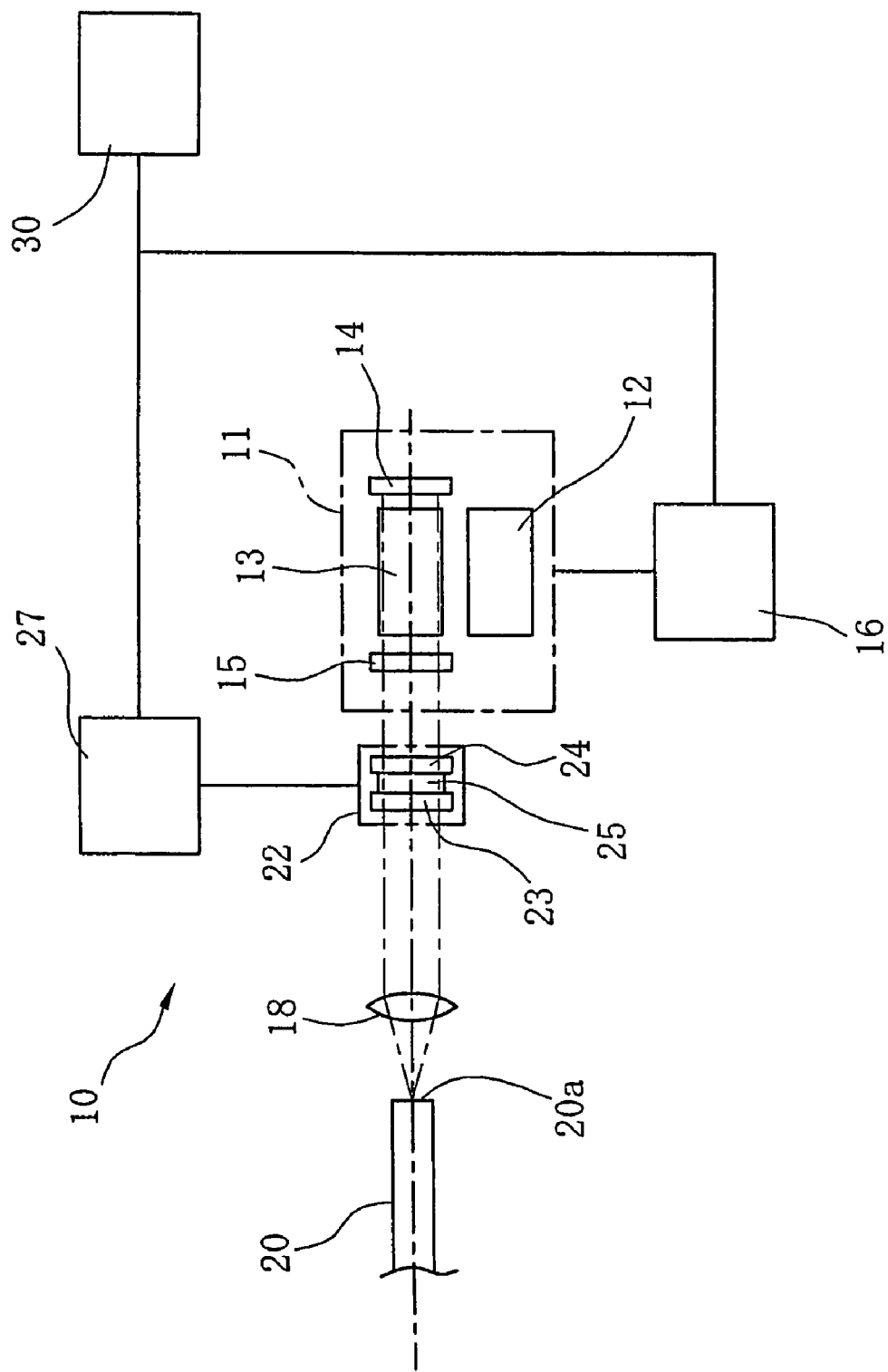
FIG. 1 is a drawing showing the configuration of processing equipment for forming a hole in the end surface of a suture needle in a method for manufacturing an eyeless suture needle of the present invention.

FIG. 1 is a drawing showing the configuration of processing equipment 10 for forming a hole in the end surface of a suture needle in a method for manufacturing an eyeless suture needle of the present invention.

A laser oscillator 11 for emitting machining laser beams has a lamp 12 and a YAG rod 13 which is excited by light from the lamp 12 and outputs the laser beams. These lamp 12 and YAG rod 13 are arranged horizontally. The lamp 12 has a bulb filled with gaseous xenon. The laser oscillator 11 is driven by a laser oscillator drive unit 16.

A total reflection mirror 14 and a half reflection mirror 15 are arranged in the vicinity of both ends of the YAG rod 13. A condensing lens 18 is arranged in the optical axis direction of the YAG rod 13, and the end surface 20a of a needle material 20 to serve as the suture needle is set in the vicinity of the focusing position of the condensing lens 18. At that time, the needle material 20 is set so that the axial center of the needle material 20 and the optical axis of the laser beam overlap accurately. In the case of a round needle, the tip part side of the needle material 20 is sharpened in a conical shape, and in the case of a square needle, the needle material 20 is made into a pyramidal shape to form an edge consisting of the ridgelines of a pyramid, and a sharp tip part. However there is also a case of a state where the tip part has not been sharpened yet.

An electric shutter 22 is provided between the half reflection mirror 15 of the above laser oscillator 11 and the condensing lens 18. The electric shutter 22 has, for example, two polarizers 23 and 24, and a crystal cell 25 interposed between the polarizers 23 and 24. The laser beam is intercepted when voltage is applied to the crystal cell 25, and the laser beam can be transmitted when the voltage is not applied. The electric shutter 22 is driven by an electric shutter drive unit 27.

The laser oscillator drive unit 16 and the electric shutter drive unit 27 are controlled by a control unit 30, and the entire equipment for hole formation is controlled by the control unit 30. A computer is used as the control unit 30.

Although illustration is omitted, a visible laser oscillator described in the patent document 2 may be provided at the opposite side of the needle material 20 of the laser oscillator 11.

When high voltage is instantaneously applied to the trigger electrode of the lamp 12, an instantaneous discharge is generated between the anode and cathode of the lamp 12. The discharge serves as a trigger, a principal current flows between the anode and the cathode, and the lamp 12 emits light.

The light of the lamp 12 is condensed and supplied to the YAG rod 13 by a reflecting mirror not shown. Within the YAG rod 13, the electrons of neodymium ions excited by the light transit to an orbital of a higher energy level, laser beams are emitted when the electrons return to a normal energy level, the laser beams are amplified while reciprocating between the total reflection mirror 14 and the half reflection mirrors 15, and then the laser beams having a large output pass through the half reflection mirror 15, and come out from the laser oscillator 11.

Figure 2:
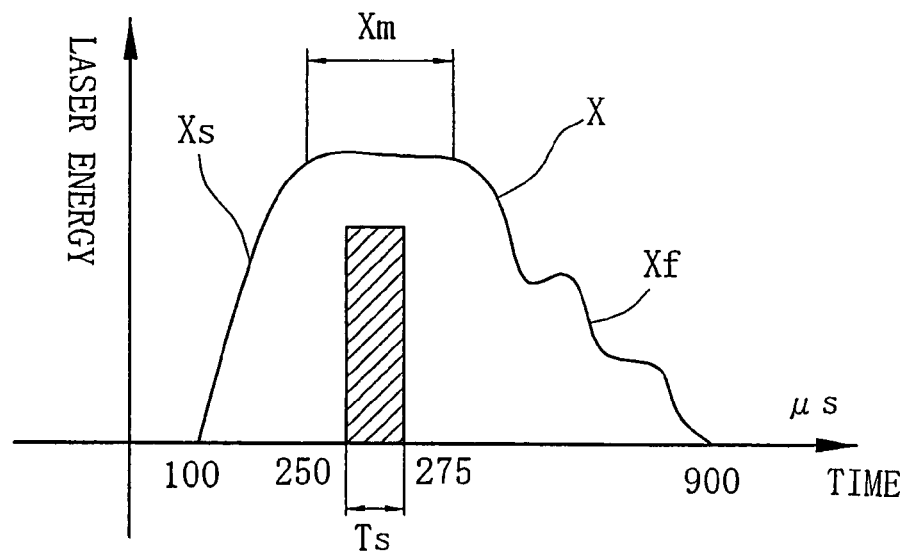
FIG. 2 is a drawing showing a state of extracting a portion used for hole formation machining from the output energy of one shot of a laser beam in a case of one minute width pulse.

The characteristics line between the output energy of one shot (one pulse) of the laser beam and time is shown by a curve X in FIG. 2. In the present example, the output of the laser beam begins to rise after 100 microseconds (μs) after trigger voltage is applied to the lamp 12, and terminates 900 microseconds after the trigger voltage application. The rising edge portion Xs and falling edge portion Xf of the laser beam output have a large output fluctuation for each shot, and the fluctuation is particularly large at the falling edge portion Xf. However a middle portion Xm is stable.

In the present invention, the stable middle portion Xm, moreover a part of middle portion is extracted from the laser beam output by using the opening and closing of the electric shutter 22 to irradiate the end surface 20a of the needle material 20 for hole formation. A hatched portion of FIG. 2 shows the portion extracted for irradiation, and Ts represents irradiation time. The height (magnitude of energy) of the hatched portion is lower than the height of Xm because the transmittance of the electric shutter 22 is less than one, and the height of the hatched portion is determined by the transmittance.

Figure 3:
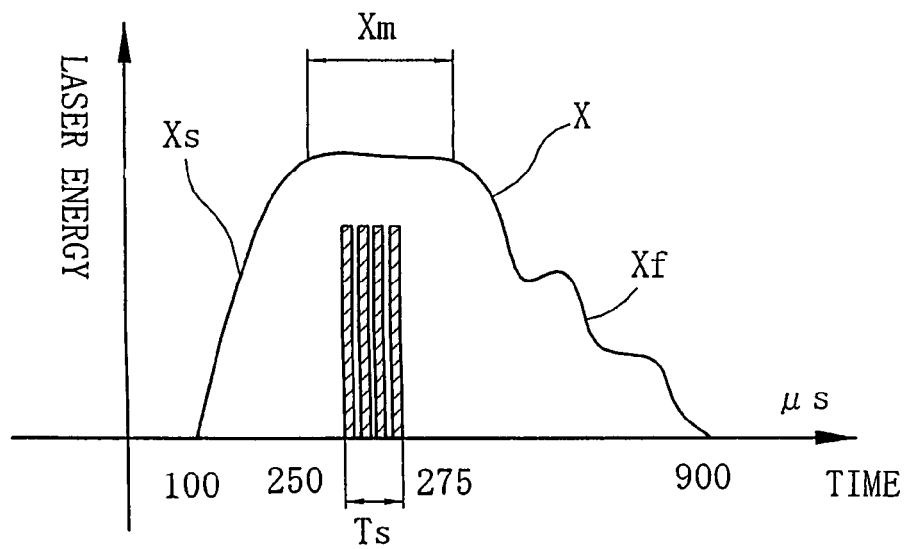
FIG. 3 is a drawing showing a state of extracting a portion used for hole formation machining from the output energy of one shot of a laser beam in a case of a plurality of minute width pulses.

FIG. 3 shows an example of dividing the extracted portion into a plurality of minute width pulses. Here, four minute width pulses are formed within the irradiation time Ts. When FIG. 3 shows the plurality of minute width pulses, it can be said that FIG. 2 shows one minute width pulse.

FIG. 4 is an enlarged sectional view showing the base end of the needle material 20 with a formed hole. The diameter D of the needle material 20 is larger by approximately 6 to 20 micrometers than the diameter $D_0$ of a suture needle 20'. The diameter $D_0$ of the suture needle 20' is less than 150 micrometers. The diameter d of a hole 21 is approximately 50 micrometers, and depth h is approximately 10 times the hole diameter and approximately 500 micrometers.

For example, assuming that the diameter $D_0$ of the suture needle 20' is 100 micrometers and the hole diameter d is 50 micrometers, the thickness of the hole 21 is 25 micrometers. Since the hole formation by the laser beam is carried out by sublimating the needle material 20 made of stainless steel at a high temperature, not only a hole portion but also the outside reach the high temperature. When the thickness is small, the outside also tends to melt. Accordingly, the thickness is preferably as thick as possible. Therefore, the diameter D of the needle material 20 is made larger than the diameter $D_0$ of the suture needle 20'. After hole formation, a thickened portion is removed by chemical polishing, electrolytic polishing, or the like, to form the suture needle 20' having the desired diameter $D_0$.

The diameter D of the needle material 20 is preferably larger by 6 to 20 micrometers than the diameter $D_0$ of the suture needle 20'. Since the diameter $D_0$ of the suture needle 20' is less than 150 micrometers, the diameter D of the needle material 20 as a workpiece is less than 170 micrometers.

First, the upper limit 20 micrometers is described. Under normal circumstances, the larger the diameter D is, the thicker the thickness is, which is preferable to precisely form a hole. However, the following problems occur with the chemical polishing.

First, in the case of the chemical polishing or the like, the entire surface of the needle material 20 is not necessarily removed uniformly, which causes variation. The variation becomes larger when the amount of polishing increases, and the shape of the needle itself is deformed. It is also possible that the thin portion and the thick portion of the external diameter of the suture needle 20' become conspicuous. The tip part of the needle may be spindly.

In the case of a suture needle with an edge, such as a triangular needle, the portion of the edge is also subjected to the chemical polishing, and when the amount of polishing exceeds 20 micrometers, the edge is rounded and loses its sharpness.

As for the hardness of the needle material 20, a place located slightly internally from the surface is the hardest portion, and places located in deeper portions become softer toward a core. Therefore, when the amount of polishing increases, the hardness deteriorates equal to or less than desired hardness.

The present inventor found out experimentally that the greatest numerical value without causing such a defect is 20 micrometers.

Next, the lower limit 6 micrometers is described. After hole formation machining by the laser beam has done the surface of the needle material 20 has irregularity formed during the manufacturing of the needle material. The irregularity is formed of scratches (die marks), small cracks, or the like caused by a dice during wire drawing machining, and the depth is approximately 1 to 2 micrometers in many cases.

On the other hand, a passive state film of chromium trioxide ($Cr_2O_3$) is formed on the surface of the stainless steel. The passive state film has thickness as extremely small as several nanometers. When being covered with the passive state film, the stainless steel resists rust.

Although the passive state film is formed also on the surface of the needle material 20 after hole formation machining, the passive state film is formed on the above-mentioned irregular surface along the irregular shape.

Therefore, when the irregularity is eliminated and flattened, the passive state film is newly formed and can cover the entire surface. For that purpose, 3 micrometers at one side, and the thickness of 6 micrometers in diameter need to be eliminated.

As a method of eliminating 6 micrometers in the above diameter, barrel processing may be adopted. However a method based on the electrolytic polishing or chemical polishing is suitable.

Although the number of minute width pulses may be suitably one, a plurality of numbers are more preferable. This is considered to be derived from the following reason. There are very small gutters lengthwise and crosswise caused by cutting each needle materials 20, lines caused by a grinding stone, or the like on the end surfaces of the needle materials 20. The first to second shots of the minute width pulse melts these surfaces, and makes the end surfaces uniform. As a result, the absorptivity of the laser beam in the end surface 20a becomes uniform, and a uniform hole with little variation can be formed by the successive minute width pulses.

When the inside of the hole was actually observed by using X-rays, the hole entrance had little deformation, there was also no adhesion of sputters, and the hole of a uniform diameter and depth was formed.

TEST EXAMPLES

Test examples of hole formation machining conducted by using the processing equipment shown in FIG. 1 are described in the following. However, the pulse width described in the following represents Ts shown in FIGS. 2 and 3. In all the test examples, the needle material diameter D is 160 micrometers, the diameter $D_0$ of the suture needle is 140 micrometers, the hole diameter d is 50 micrometers, and the depth h of the hole is 500 micrometers.

TABLE 1

| No. | Pulse width | Minute width | Evaluation | Remarks |
| --- | --- | --- | --- | --- |
| 1 | 80–100 | 6 | x | A hole longer by 2.5 times than normal is formed, and the hole is clogged. |
| 2 | 40–50 | 6 | x | A hole longer by 2.5 times than normal is formed, and the hole is clogged. |
| 3 | 40–50 | 6 | x | A focus is shifted by 3 mm. A hole is short but pierced. |

TABLE 1-continued

| No. | Pulse width | Minute width | Evaluation | Remarks |
| --- | --- | --- | --- | --- |
| 4 | 30–37.5 | 6 | x | A hole is deep and clogged. |
| 5 | 20–25 | 6 | ○ | Satisfactory. |
| 6 | 30–37.5 | 3 | Δ | There is no hole clogging, a little swelling, and usable if adjusted. |
| 7 | 30–35 | 3 | Δ | There is some hole clogging, but usable if adjusted. |
| 8 | 20–25 | 3 | ○ | Satisfactory. |
| 9 | 30–35 | 1 | Δ | There is variation, but usable if defects are eliminated. |
| 10 | 20–25 | 1 | ○ | There is a little swelling in the inner part of a hole, and variation, but the hole is practically satisfactory. |

The above result shows that a pulse width of 35 microseconds or less is preferable independent of the number of minute pulses, further 25 microseconds or less is considered to be more preferable. The number of minute pulses of one may be sufficient. However, when a plurality of minute pulses are used, variation is reduced, and a still more satisfactory result has been confirmed.

What is claimed is:

1. A method for manufacturing an eyeless suture needle by forming a hole for inserting and fixing one end of a suture thread by caulking in a proximal end surface of the eyeless suture needle made of stainless steel, comprising the steps of:
   irradiating the end surface of a needle material, which surface has irregularities formed therein during manufacture, the needle material having a diameter that is 6 to 20 micrometers greater than a desired needle diameter of the suture needle of less than 150 micrometers, with one shot of a laser beam having a total pulse width equal to or less than 35 microseconds that is extracted from one shot of a laser beam emitted from a laser oscillator with an electronic shutter to form a hole therein; and
   subsequently, removing a portion of the needle material that is thicker than the desired needle diameter.

2. A method for manufacturing an eyeless suture needle by forming a hole for inserting and fixing one end of a suture thread by caulking in a proximal end surface of the eyeless suture needle made of stainless steel, comprising the steps of:
   irradiating the end surface of a needle material having a desired needle diameter of less than 150 micrometers with one shot of a laser beam divided into a plurality of pulses and having a total pulse width of equal to or less than 35 microseconds to form a hole therein,
   said laser beam being extracted from one shot of a laser beam emitted from a laser oscillator; and
   with the first one or two pulses, melting unevenness in the end surface of the needle material caused by cutting or grinding to give the end surface a uniform flatness, whereby a clean hole can be formed by succeeding pulses following the first one or two pulses.

* * * * *